US007015006B1

(12) United States Patent
Glen et al.

(10) Patent No.: US 7,015,006 B1
(45) Date of Patent: Mar. 21, 2006

(54) DIAGNOSTIC TEST

(75) Inventors: Alastair Campbell Agnew Glen, Glasgow (GB); Donald John Mcdonald, Glasgow (GB)

(73) Assignee: Amarin Neuroscience Limited, Stirling (GB)

( * ) Notice: Subject to any disclaimer, the term of this patent is extended or adjusted under 35 U.S.C. 154(b) by 0 days.

(21) Appl. No.: 09/936,198

(22) PCT Filed: Mar. 8, 2000

(86) PCT No.: PCT/GB00/00845

§ 371 (c)(1),
(2), (4) Date: Sep. 10, 2001

(87) PCT Pub. No.: WO00/54052

PCT Pub. Date: Sep. 14, 2000

(30) Foreign Application Priority Data

Mar. 9, 1999 (GB) .................................. 9905417
Aug. 23, 1999 (GB) .................................. 9919952

(51) Int. Cl.
*C12Q 1/44* (2006.01)
*G01N 33/573* (2006.01)
*G01N 33/68* (2006.01)

(52) U.S. Cl. .................... 435/7.25; 435/7.4; 435/19; 436/63; 436/86

(58) Field of Classification Search ............... 435/7.25, 435/7.4, 19; 436/63, 86
See application file for complete search history.

(56) References Cited

U.S. PATENT DOCUMENTS

| 5,279,957 A | 1/1994 | Gross |
| 5,354,677 A | 10/1994 | Knopf et al. |
| 5,527,698 A | 6/1996 | Knopf et al. |
| 5,593,878 A | 1/1997 | Knopf et al. |

FOREIGN PATENT DOCUMENTS

| EP | 0 476 849 A2 | 8/1991 |
| RU | 2009509 | 3/1994 |

OTHER PUBLICATIONS

Adachi I. et al., "Phospholipase $A_2$ of Chicken Erythrocyte Membranes", Arch. Biochem. and Biophys., 1983, 226(1): 118-24.
Clark J.D. et al., "A Novel Arachidonic Acid-Selective Cytosolic $PLA_2$ Contains a $Ca^{2+}$-Dependent Translocation Domain with Homology to PKC and GAP", Cell, 1991, 65:1043-51.
Database WPI, "Predicting the course of psoriasis by determining the phospholipase $A_2$ activity in the erythrocytes and blood plasma", Derwent Publications Ltd., 1994, London.
Gattaz W.F. et al., "Increased Plasma Phospholipase-A2 Activity in Schizophrenic Patients: Reduction after Neuroleptic Therapy", Biological Psychiatry, 1987, 22:421-6.
Hudson C.J. et al., "Phospholipases: in search of a genetic base of schizophrenia", Prostaglandins, Leukotrienes and Essential Fatty Acids, 1996, 55(1&2):119-22.
Pickard R.T. et al., "Molecular Cloning of Two New Human Paralogs of 85-kDa Cytosolic Phospholipase $A_2$", Journal of Biological Chemistry, 1999, 274(13):8823-31.
Tuzhilin S.A. et al., "The method for phospholipase A determination in blood serum", Laboratornoe Delo, 1975, 6:334-5.
Zhu X. et al., "Quantitation of the cytosolic phospholipase $A_2$ (typeIV) in isolated human peripheral blood eosinophils by sandwich-ELISA", Journal of Immunological Methods, 1996, 199:119-26.
Paysant et al., Action Enzymatique Des Globules Bouges De Rat Sur Le Phosphatidyglycerol, Bull. Soc. Chim. Biol, 1967, 49 No. 2, pp. 169-176.
Pasyant et al., Phospholipase A Des Globules Rouges Chez L'Homme,Action Sur Les Phospholipides Endogenes Et Exogenes, Bull. Soc. Chim. Biol., 1970 52 No. 11 pp. 1257-1269, Abst Only.
Kramer et al., Some Characteristics of a Phospholipase $A_2$ From Sheep Red Cell Membranes, Biochimica et Biophysica Acta, (1974) 373, p. 404-415.
Jimeno-Abendano et al.,Purified Phospholipase $A_2$ From Sheep Ereythrocyte Membrane. Preferential Hydrolysis According to Polar Groups and 2-Acyl Chains,Biochimica et Biophysica Acta, 573 (1979), pp. 266-275.

*Primary Examiner*—David Saunders
(74) *Attorney, Agent, or Firm*—Klauber & Jackson

(57) ABSTRACT

An assay for detecting type IV cytosolic phospholipase $A_2(cPLA_2)$ or a protein immunologically homologous to type IV $cPLA_2$, the assay comprising use of red blood cells, particularly for use in the diagnosis of a disease in which dysfunction of cell signalling systems involving highly unsaturated fatty acids is implicated.

24 Claims, 4 Drawing Sheets

DIAGNOSTIC TEST

The present invention is concerned with identification of proteins of the cytosolic phospholipase $A_2$ enzyme and the applications thereof, particularly in diagnosis, treatment monitoring and drug development.

Phospholipase $A_2$ ($PLA_2$) enzymes are generally characterised by their capacity to catalyse the hydrolysis of the Sn2 acyl-ester bond of glycerophosphate to release free fatty acid (Mayer R. J. and Marshall L., *FASEB J,* 7, 339–348; Dennis E. A., Ed., Phospholipase $A_2$ Methods in Enzymology, 1991, 197, 359–433). The scientific literature recognises different types of $PLA_2$ enzyme (Dennis E. A., *Trends Biochem. Sci.,* 22, 1–2). Types I, II and III are referred to as secretory phospholipase $A_2$ ($sPLA_2$) enzymes. Secretory phospholipase $A_2$ enzymes have a molecular weight of approximately 14 kDa, are found extracellularly and have been recognised in plasma.

The type IV $PLA_2$ enzyme is referred to as cytosolic phospholipase $A_2$ ($cPLA_2$). It features a calcium binding domain, termed the C2 domain, and its phospholipase activity is highly selective for highly-unsaturated fatty acids, particularly arachidonic acid, present in the Sn2 acyl-ester glycerophosphate bond. Its ability to release arachidonic acid from cell membrane phospholipids sets it in a key position for the regulation of the supply of arachidonate and subsequent action in cell messenger processes.

A further type of $PLA_2$ enzyme is the type VI enzyme which is also a cytosolic $PLA_2$ enzyme, but which does not possess the high selectivity for arachidonic acid in the Sn2 position of glycerophospate for phospholipid acyl ester hydrolysis (Tang J. et al., *J. Biol. Chem.,* 272, 1997, 8567–8575). It is termed $iPLA_2$ in recognition that it is independent of calcium level for its catalytic activity.

The type IV arachidonate-selective $cPLA_2$ enzyme has been identified in a number of tissues including human monocytes (Clark J. D. et al., *Cell,* 65, 1991, 1043–1051; Kramer R. M. et al., *J. Biol. Chem.,* 266, 1991, 5268–5272) and human platelets (Takayama K. et al., *FEBS,* 282, 1991, 326–330).

The amino acid sequence of type IV $cPLA_2$ has been determined for the enzyme purified from human monocyte (U937) cells (Clark J. D. et al., *Cell,* 65, 1991, 1043–1051). Type IV $cPLA_2$ found in U937 cells has an amino acid sequence which is 749 amino acids long. This sequence shows a region of homology with a limited number of other proteins including protein kinase C (PKC), GTPase activating protein (GAP), phospholipase C and synaptic vesicle protein p65. The points of homology occur towards the N-terminal end of the protein in the so-called calcium-binding portion which is at or around amino acids 36 to 81 of the sequence (counting from the NH2 terminal end) (Nalefski et al., *J. Biol. Chem.,* 269, 18239–18249). There are no known areas of sequence homology between other mammalian proteins and type IV $cPLA_2$ amino acids 82 to 749, apart from a sequence from amino acids 129 to 135 shared with pulmonary surfactant protein C (Clark et al., *J. Lipid Mediators Cell Signalling,* 12, 83–117) and two recently reported cytosolic phospholipase $A_2$ enzymes designated $cPLA_2\beta$ and $cPLA_2\gamma$ (R. T. Pickard et al, *J. Biol. Chem.,* 1999, 274, 8823–8831). These are proteins different from the $cPLA_2$ enzyme isolated from human U937 monocytes (which now may be designated as $cPLA_2\alpha$). The $cPLA_2\alpha$, $\beta$ and $\gamma$ sequence homology is limited to five amino acids found in $cPLA_2\alpha$ at position serine 228 to tryptophan 232.

The catalytic active centre of type IV $cPLA_2$ has been reported as being located in a peptide sequence comprising amino acid 228 (Clark J. D. et al., *J. Lipid Mediators Cell Signalling,* 12, 83–117) and has recently been described as being dependent for its function on the proximity of two amino acids brought together in the folded tertiary structure of the molecule, serine 228 and aspartate 549 (Dessen A. et al., *Cell,* 1999, 97, 349–360).

Previous observations of $PLA_2$ enzymes in the circulation have been directed at measurements in serum or plasma by substrate assay methods and have not characterised the type of the enzyme involved (Thuren T. et al., *Clin. Chem.,* 31, 1985, 714–717; Gattaz W. F. et al., *Biol. Psychiatry,* 22, 1987, 421–426; Gattaz W. F. et al., *Biol. Psychiatry,* 28, 1990, 495–501). Serum and plasma $PLA_2$ enzymes show increased activity relative to normal control subjects in the human disease schizophrenia, although again the $PLA_2$ type of the enzyme responsible has not been characterised. To date, there has been no identification of cytosolic phospholipase $A_2$ type IV protein either in or attached to red cells either physiologically or in pathology.

It has now been found that type IV $cPLA_2$ proteins or proteins immunologically homologous to type IV $cPLA_2$ can be detected in or on circulating red blood cells. The detection and assay of these $cPLA_2$ proteins has application in the diagnosis of disease, in the monitoring of the patient response to treatment and in the development of drugs which influence the activity or concentration of $cPLA_2$. Recognition that these $cPLA_2$ proteins may be detected in or on red blood cells provides a simple and convenient method of assaying for the $cPLA_2$ level.

BRIEF DESCRIPTION OF THE DRAWINGS

FIG. 1 depicts western blots.

FIG. 3 depicts a frequency histogram of type IV $cPLA_2$ levels.

Figure 1A:
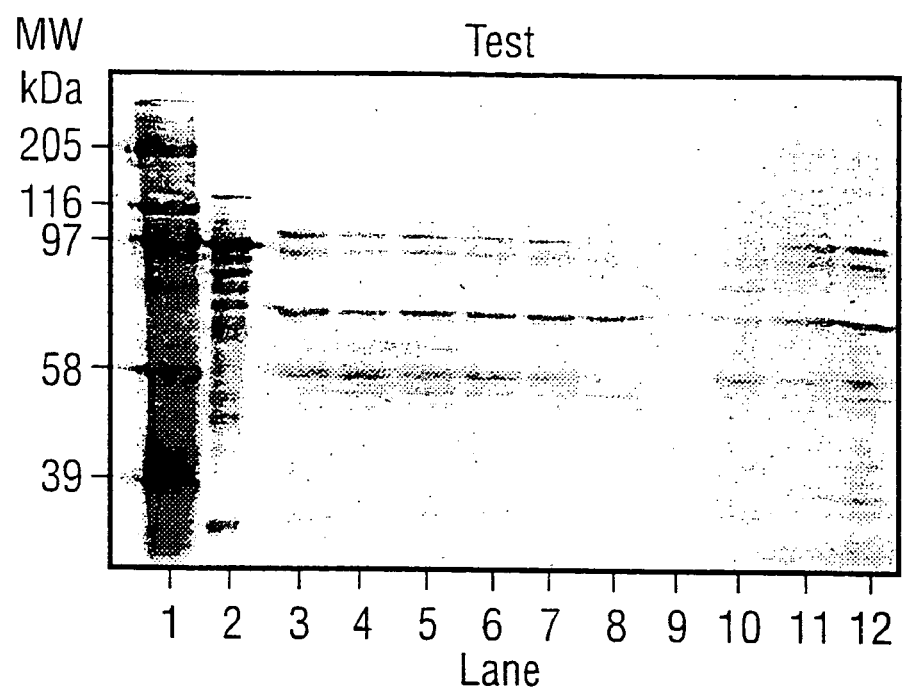
FIG. 1a depicts a western blot to identify type IV $cPLA_2$ antigen using a rabbit polyclonal antibody raised against mid-molecule type IV $cPLA_2$ and a swine anti-rabbit IgG antibody coupled to horseradish peroxidase. Lane 1: molecular weight markers. Lane 2: cell cytosol from insect cells infected with baculovirus expressing type IV $cPLA_2$. Lanes 3–12: samples of red cell hemolysates from schizophrenic patients taking clozapine (lanes 4, 7, 9 and 10), schizophrenic patients taking neuroleptic drugs (lanes 8 and 12), and control patients (lanes 3, 5, 6 and 11).

According to a first aspect of the present invention, there is provided an assay for detecting type IV cPLA$_2$ or a protein immunologically homologous to type IV cPLA$_2$, the assay comprising use of red blood cells. In a second aspect of the invention, there is provided an assay for quantifying the level of type IV cPLA$_2$ or a protein immunologically homologous to type IV cPLA$_2$ in a sample of red blood cells. The assay may be performed on a sample of whole blood or on a sample of red blood cells after separation thereof from whole blood.

As used herein, the term "a protein immunologically homologous to type IV cPLA$_2$" means a protein that binds specifically to an antibody or antibodies that recognise an epitope or epitopes from any part of type IV cPLA$_2$ protein from human monocyte (U937) cells, and preferably an epitope or epitopes from amino acids 82 to 749 of type IV cPLA$_2$ protein from human monocyte (U937) cells. In a preferred embodiment of the invention, the term "a protein immunologically homologous to type IV cPLA$_2$" means a protein that binds specifically to an antibody or antibodies that recognise an epitope or epitopes from a peptide sequence or sequences which comprise the catalytic active centre of type IV cPLA$_2$ protein from human monocyte (U937) cells. In a further preferred embodiment, the term "a protein immunologically homologous to type IV cPLA$_2$" means a protein that binds specifically to an antibody or antibodies that recognise an epitope or epitopes from the peptide sequence of amino acids 241 to 260 of type IV cPLA$_2$ protein from human monocyte (U937) cells.

In an alternative embodiment, the term "a protein immunologically homologous to type IV cPLA$_2$" means a protein that binds specifically to an antibody or antibodies raised against an epitope or epitopes from any part of type IV cPLA$_2$ protein from human monocyte (U937) cells or a synthetic peptide matching the sequence of type IV cPLA$_2$ protein from human monocyte (U937) cells. In a preferred alternative embodiment, the term "a protein immunologically homologous to type IV cPLA$_2$" means a protein that binds specifically to an antibody or antibodies raised against an epitope or epitopes from amino acids 82 to 749, and preferably an epitope or epitopes from a peptide sequence or sequences which comprises the catalytic active centre, of type IV cPLA$_2$ protein from human monocyte (U937) cells or a synthetic peptide matching the sequence of amino acids 82 to 749, and preferably a sequence or sequences which comprises the catalytic active centre, of type IV cPLA$_2$ protein from human monocyte (U937) cells. In a further alternative embodiment, the term "a protein immunologically homologous to type IV cPLA$_2$" means a protein that binds specifically to an antibody or antibodies raised against an epitope or epitopes from the peptide sequence of amino acids 241 to 260 of type IV cPLA$_2$ protein from human monocyte (U937) cells, or a synthetic peptide matching the sequence of amino acids from the peptide sequence of amino acids 241 to 260 of type IV cPLA$_2$ protein from human monocyte (U937) cells.

According to a third aspect of the present invention, there is provided a method of diagnosis of a disease in which dysfunction of cell signalling systems involving highly unsaturated fatty acids is implicated, said method comprising the detection of type IV cPLA$_2$ protein or a protein immunologically homologous to type IV cPLA$_2$ in or on red blood cells. The method may further comprise the step of determining the level of type IV cPLA$_2$ protein or a protein immunologically homologous to type TV cPLA$_2$ in or on red blood cells and, optimally, comparing this level with a control level.

As used herein, the term "highly unsaturated fatty acids" includes all fatty acids released by action of the type IV cPLA$_2$ enzyme. In an embodiment of the invention the term "highly unsaturated fatty acids" includes fatty acids having 3 or more carbon—carbon double bonds. In particular, the term includes the essential fatty acids, particularly the fatty acids of the group comprising dihomogammalinolenic acid (DGLA; 8,11,14-eicosatrienoic acid), arachidonic acid (AA; 5,8,11,14-eicosatetraenoic acid), adrenic acid (7,10,13,16-docosatetraenoic acid), 4,7,10,13,16-docosapentaenoic acid, stearidonic acid (SA; 6,9,12,15-octadecatetraenoic acid), 8,11,14,17-eicosatetraenoic acid, eicosapentaenoic acid (EPA; 5,8,11,14,17-eicosapentaenoic acid), docosapentaenoic acid (DPA; 7,10,13,16,19 docosapentaenoic acid) and docosahexaenoic acid (DHA; 4,7,10,13,16,19-docosahexaenoic acid).

According to a fourth aspect of the invention, there is provided a method of monitoring the effectiveness of medication administered to a patient suffering from a disease in which dysfunction of cell signalling systems involving highly unsaturated fatty acids is implicated, said method comprising the detection of type IV cPLA$_2$ protein or a protein immunologically homologous to type TV cPLA$_2$ in or on red blood cells. The method may, for example, comprise the steps of administering to a patient a compound to be tested, determining the level of type IV cPLA$_2$ protein or a protein immunologically homologous to type IV cPLA$_2$ in or on red blood cells and, optimally, comparing this level with a control level or with a level or levels determined at an earlier stage of the medication regime or before the medication regime commenced.

According to a fifth aspect of the invention, there is provided a method of drug development for a disease in which dysfunction of the cell signalling systems involving highly unsaturated fatty acids is implicated, said method comprising the detection of type IV cPLA$_2$ protein or a protein immunologically homologous to type IV cPLA$_2$ in or on red blood cells. The method may, for example, be used in the screening of compounds for use in the treatment of a disease in which dysfunction of cell signalling systems involving highly unsaturated fatty acids is implicated, the method comprising the steps of administering to a patient or test animal a compound to be tested, determining the level of type IV cPLA$_2$ protein or a protein immunologically homologous to type IV cPLA$_2$ in or on red blood cells and, optimally, comparing the level with a control level.

The invention is particularly concerned with diseases in which dysfunction of cell signalling systems involving arachidonic acid, dihomogammalinolenic acid, eicosapentaenoic acid, docosapentaenoic acid and/or docosahexaenoic acid is implicated. More particularly, the invention is concerned with diseases in which dysfunction of cell signalling systems involving arachidonic acid is implicated.

The disease conditions in which the identification of type IV cPLA$_2$ proteins or proteins immunologically homologous to type IV cPLA$_2$ in or on red cells may be useful include:
1) schizophrenia, in which increased cPLA$_2$ expression and activity is a proposed mechanism in disease development;
2) bipolar or manic depressive illness, in which cPLA$_2$ abnormality may be present;
3) cachexia, in which tumour necrosis factor promotes cPLA$_2$ activity;
4) brain injury, including stroke and mechanical injury, in which cPLA$_2$ may be released from damaged membranes or as part of the process of apoptosis;
5) dyslexia, in which abnormal cPLA$_2$ activity may be present; and
6) any other disease or disease process in which type IV cPLA$_2$ activity or concentration is increased or decreased from normal levels, particularly a disease or disease process in which type IV cPLA$_2$ activity or concentration is increased.

The assays and methods of the invention may comprise the steps of collecting a sample of blood from a subject, and detecting the proteins ex vivo. Preferably, the assays and methods further comprise one or more of the steps of separating the red cells from the other blood components, disrupting the red cells by a method such as sonication, nitrogen cavitation, freezing or lysis, and detecting the proteins either directly or following a protein separation technique. Another application for the assays and methods of the invention include their employment on whole blood, with or without the requirement of prior separation of the red cells, and such applications would include, for example, a near-patient testing diagnostic strip, cartridge, or device.

In a preferred embodiment, the assays and methods of the invention comprise the detection in or on red blood cells of one or more proteins from one or more of three particular groups of proteins. The proteins are grouped by apparent molecular weight as measured using sodium dodecyl sulphate polyacrylamide gel electrophoresis (SDS PAGE) with western blot and can be designated as follows:

Group A, comprising one or more proteins of apparent molecular weight in the range of 80 to 110 kDa, particularly in the range of 90 to 105 kDa;
Group B, comprising more or more proteins of apparent molecular weight in the range of 70 to 80 kDa;
Group C, comprising one or more proteins of apparent molecular weight in the range of 50 to 60 kDa.

It is considered that the proteins in a given group may be structurally related, small variations in apparent molecular weight between the proteins in a given group possibly being due to the extent of phosphorylation. However, it is not intended that the scope of the invention be limited by this theory. Variations in apparent molecular weight among proteins of a given group may simply be due to variations in the length of the amino acid sequence of the protein or protein fragment.

These proteins react immunologically with antibodies to cPLA$_2$. The proteins can be identified by an antibody or antibodies which react with an epitope or epitopes present in a region of the type IV cPLA$_2$ protein which does not share sequence homology with other proteins, for example a region other than the calcium-binding portion of the protein. The proteins can also be identified by using a first antibody (a "capture antibody") which reacts with an epitope or epitopes present in a sequence having homology with other proteins, for example, the calcium binding portion of the type IV cPLA$_2$ protein, and a second antibody (a "detection antibody") which reacts with an epitope or epitopes in a region of the protein which does not have homology with other proteins in order to provide the necessary specificity. Protein detection and identification is discussed in more detail below.

It is considered that the proteins or protein fragments isolated from in or on red blood cells may be the same as the type TV cPLA$_2$ protein, or fragments thereof, found in human monocyte (U937) cells. Thus, it is considered that the proteins having apparent molecular weights in the range of 80 to 110 kDa (particularly 90 to 105 kDa), in the range 70 to 80 kDa and in the range 50 to 60 kDa may be either intact type TV cPLA$_2$ or major components of type IV cPLA$_2$. However, it is not intended that the scope of the invention be limited by this theory.

According to a further aspect of the invention there is provided a protein obtainable by isolation from red blood cells, said protein being immunologically homologous to type IV cPLA$_2$. Said protein may exist in the body in the form of a protein having a molecular weight in the range 80 to 110 kDa (and particularly in the range of 90 to 105 kDa) or in the form of a protein having a molecular weight in the range 70 to 80 kDa or in the form of a protein having a molecular weight in the range 50 to 60 kDa.

Protein Separation

The type IV cPLA$_2$ proteins or proteins immunologically homologous to type IV cPLA$_2$ proteins are typically separated from the other proteins of red blood cells by SDS PAGE but a variety of other protein separation techniques may be used, including native polyacrylamide gel electrophoresis and various column separation techniques such as fast protein liquid chromatography and variants of Sepharose or other commercially available columns. Two dimensional electrophoretic techniques may also be used. As noted above, prior protein separation is not always necessary and the type IV cPLA$_2$ proteins or proteins immunologically homologous to type IV cPLA$_2$ may be detected in red cells by immunological means without the necessity of prior protein separation.

Protein Detection

The detection of type IV cPLA$_2$ proteins and/or proteins immunologically homologous to type IV cPLA$_2$ can be achieved by a wide range of protein detection procedures including:
1) enzyme linked immunoassay, radioimmunoassay, luminescence immunoassay, fluorescence immunoassay or any other variant of competitive or tagged antibody immunoassay, including biosensor technology (evanescent wave optical biosensor);
2) immunofluoroescence or other immunoassay on red blood cells in smears, droplets, films, fixed histological sections or tissue samples;
3) in vitro tests in which the protein is recognised by a specific polyclonal or monoclonal antibody and the specific antibody is itself recognised in a Coombs-type test; and
4) enzymic substrate assay of type IV cPLA$_2$ proteins utilising natural or artificial phospholipid substrates together with specific inhibitors of the other phospholipase enzymes.

In one embodiment of the invention, protein detection is achieved using diagnostic strips, cartridges or devices suitable for near-patient testing which detect the proteins using any of the above techniques or any other technique known in the art.

In a preferred embodiment, the proteins are detected using either a polyclonal or a monoclonal antibody or a combination thereof. Table 1 provides examples of antibodies suitable for use in the assays of the present invention for the detection of type IV cPLA$_2$ proteins or proteins immunologically homologous to type IV cPLA$_2$.

Suitable antibodies or combinations of antibodies for use in the present invention can also include one or more of, for example, a polyclonal antibody raised against an epitope of the peptide chain comprising amino acids 730 to 749 of type IV cPLA$_2$ from U937 cells, or an extended or different amino acid sequence from the C-terminal end of the molecule; an antibody or antibodies raised against a mid-molecule peptide sequence or sequences which comprise the catalytic active site of type IV cPLA$_2$ from U937 cells; an antibody or antibodies raised against an epitope from the N-terminal part of the sequence (amino acids 1 to 216); and an antibody or antibodies raised against another epitope or epitopes from the amino acid sequence of type IV cPLA$_2$ protein from U937 cells between amino acids 82 and 749.

EXAMPLES

I. Collection of Samples

The collection of samples for protein separation and detection were performed as follows:

1) Samples of venous blood (4 to 6 ml) were collected by venepuncture using EDTA at standard concentration for anticoagulation (Vacutainer® or Starstedt Monovette ®). Other appropriate anticoagulants known to persons skilled in the art may also be used.)
2) Within 3 minutes of the sample being withdrawn, protease inhibitors were added. To the 4 or 6 ml volume of blood were added 0.5 ml of a protease inhibitor cocktail, freshly prepared, as follows:

To 3 mls of Aprotinin (Trasylol®) concentration 10.000 Kallikrein inactivator units per ml was added 2 mg phenylmethylsulphonyl fluoride (PMSF) and 0.5 mg

TABLE 1

| ANTIGEN | TYPE | PRODUCTION METHOD | SOURCE | DETECTS cPLA$_2$-LIKE PROTEINS IN RED CELLS |
| --- | --- | --- | --- | --- |
| Human type IV cPLA$_2$ synthetic peptide from mid molecule | Polyclonal IgG | Raised in Rabbits | Cayman Chemical | Yes |
| Human type IV cPLA$_2$ synthetic peptide of a 24 amino acid sequence from the C-terminal domain | Polyclonal IgG | Raised in Sheep | The Binding Site | Yes |
| Human cPLA$_2$ synthetic peptide to amino terminal (amino acids 1–216) | Monoclonal IgG | Mouse | Chemicon International Inc. | Yes |
| Human type IV cPLA$_2$ synthetic peptide mid molecule sequence (amino acids 241 to 260)[a] | Polyclonal IgG | Raised in Sheep | In-house production | Yes |

[a]: This antibody is prepared using as antigen a synthetic peptide comprising amino acids 241 to 260 of type IV cPLA$_2$ (as found in human monocytes, U937 cells), coupled to ovalbumin. The antigen is injected into sheep with Freunds adjuvant combining the intra-muscular and subcutaneous routes in standard approved protocol. The resulting antiserum was purified initially using Protein A and further purified using an affinity matrix carrying the peptide 241 to 260 not coupled to ovalbumin, to provide an affinity purified IgG antibody.

The recognition of type IV cPLA$_2$ proteins or proteins immunologically homologous to type IV cPLA$_2$ in an accessible component of blood opens the way to their use as follows:

a) Diagnostic use by direct immunoassay of their level.
b) Use in a diagnostic sense indirectly as part of a Coombs-type test.
c) Recognition by immunofluorescence on or in red blood cells on slide or smear or tissue preparation.
d) Use in an immune precipitation or other reaction to recognise type IV cPLA$_2$ proteins or proteins immunologically homologous to type IV cPLA$_2$ in whole blood samples in near-patient testing.
e) Use in monitoring of treatments which are directed to suppress PLA$_2$ activity or concentration.
f) Use in the research for agents which suppress PLA$_2$ activity or concentration for drug discovery.

The invention will now be described in detail with reference to the following examples. It will be appreciated that the invention is described by way of example and modification of detail may be made without departing from the scope of the invention.

leupeptin. Other appropriate inhibitor preparations known to persons skilled in the art may also be used.

3) The whole blood sample was then centrifuged, at 3000 rpm (1,000 g), for 10 minutes. Plasma was removed and the layer of white cells and platelets (the buffy coat) removed by plastic pipette, to leave the red cells in the tube.
4) A volume of ice cold phosphate buffered saline PBS pH 7.4 or other appropriate buffer, equal in volume to the red cells was added and red cells and buffer were mixed by inversion.
5) The cells in buffer were then centrifuged, at 1,000 g, repeating steps 3 and 4 three times, providing washed red cells.
6) The washed red cells were frozen in 0.5 ml aliquots were suspended in 0.5 ml of buffer, prepared as follows: 0.37 g KCl, 0.74 g disodium EDTA, 3.0 g Tris, 9 g NaCl in 1 liter of water, adjusted to pH 7.4 with HCl. (Kramer et al. *J. Biol. Chem.* 266, 5268–5272). The washed red cells may alternatively be frozen directly as packed cells.

In a simplified procedure, blood is collected into an EDTA vacutainer, centrifuged at 3000 rpm (1000 g) for 10 minutes, the plasma and the buffy coat removed by aspiration and the packed red cells stored frozen.

7) These samples were stored frozen at −80° C. or used directly after brief freezing to provide lysis for SDS polyacrylamide gel electrophoresis or for immunoassay in a calibrated assay. Where packed cells are stored frozen prior to use they are thawed into the buffer described in step (6) above.

Where the simplified procedure is employed, protease inhibitor is included in the buffer added to the red cells for the thawing process in the form of one tablet of COMPLETE™ protease inhibitor (Boehringer Mannhein) per 200 ml of buffer.

I. Protein Separation and Detection using SDS PAGE

Protein separation and detection was achieved using SDS PAGE as described below.

In SDS PAGE, the sample was treated with a volume of sample buffer, comprising Tris buffer pH 6.8 containing 6% SDS, 0.5% dithiothreitol and 20 ml glycerol per 100 ml. (Alternative buffers known to persons skilled in the art may be used). Lysate was added to give a 4-fold or greater dilution of the lysate in sample buffer. The sample was transferred to the standard SDS 7.5% polyacrylamide gel for electrophoresis. After electrophoresis the proteins were transferred from the gel to a membrane by electroblotting.

The test membrane was reacted with polyclonal antibody to mid-molecule type IV $cPLA_2$ raised in rabbit and then anti rabbit IgG antibody raised in swine which has been coupled to horse raddish peroxidase to demonstrate the presence of the $cPLA_2$ antigen. The blank membrane was reacted with anti rabbit IgG antibody raised in swine which has been coupled to horse raddish peroxidase. Any bands observed on the blank membrane are due to the presence of antigens other than the $cPLA_2$ antigen.

Figure 1B:
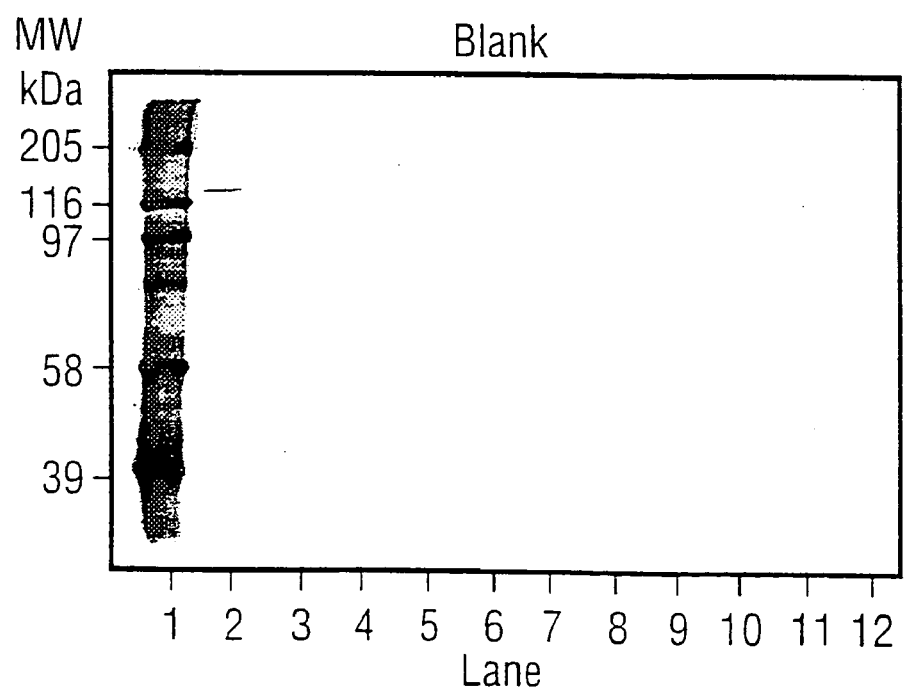
FIG. 1b depicts a western blot to identify antigens other than type IV $cPLA_2$ and a swine anti-rabbit IgG antibody coupled to horseradish peroxidase. Lane 1: molecular weight markers. Lane 2: cell cytosol from insect cells infected with baculovirus expressing type IV $cPLA_2$. Lanes 3–12: samples of red cell hemolysates taken schizophrenic patients taking clozapine (lanes 4, 7, 9 and 10), schizophrenic patients taking neuroleptic drugs (lanes 8 and 12) and control patients (lanes 3, 5, 6 and 11).

FIG. 1a and 1b show two western blot analyses (FIG. 1a is the test membrane; FIG. 1b is the blank membrane) on the following samples:

Lane 1: Molecular weight markers

Lane 2: Cell cytosol from insect cells infected with Baculovirus expressing type TV $cPLA_2$.

Lanes 3–12: Patient samples. The samples were taken from schizophrenic patients on clozapine (lanes 4, 7, 9 and 10), schizophrenic patients on neuroleptic drugs (lanes 8 and 12) and from control patients (lanes 3, 5, 6 and 11).

The patient samples on the test membrane show three band types grouped by molecular weight as described above:

Group A: one band is observed above the 97 kDa molecular weight marker, having a molecular weight of about 100 to 105 kDa, and one band is observed below the 97 kDa molecular weight marker, having a molecular weight of about 90 to 95 kDa;

Group B: a single band is observed with molecular weight around 70 kDa;

Group C: three bands are observed with molecular weights around 60 kDa. Two of the bands in this molecular weight group are believed to be type IV $cPLA_2$ proteins. The most distinct of these also appears on the blank membrane, has a less specific immunological response and may not be a type IV $cPLA_2$ protein.

In summary, the red cell lysates contained five proteins, two in the range of about 90 to about 105 kDa, one in the range of about 70 to about 80 kDa, and two in the range of about 50 to about 60 kDa, which reacted specifically in SDS PAGE western blot analysis with polyclonal antibody prepared against mid-molecule sequences of type IV $cPLA_2$.

As noted above the bands grouped in Groups A, B and C may represent, respectively, the intact type IV $cPLA_2$ molecule in differing stages of phosphorylation and two groups of peptide sequences of type IV $cPLA_2$ proteins which have lost amino acids by protein degradation. However, as stated above, it is not intended that the scope of the invention be limited by this theory. The bands grouped in Groups A, B and C could also represent intact type IV $cPLA_2$ and fragments of type IV $cPLA_2$ differing in the length of amino acid sequence.

III. Protein Detection Using Enzyme Linked Immunoassay (ELISA)

Immunoassay, specifically enzyme linked immunoassay (ELISA), was also used to detect red cell type IV $cPLA_2$ proteins or proteins immunologically homologous to type IV $cPLA_2$. This method uses a luminescence end point for protein detection.

Samples are collected and prepared as hereinbefore described. Samples of red cells for analysis were stored at −80° C.

The following reagents are required for ELISA:

1) Coating buffer, pH 9.6
   1.59 g sodium carbonate, 2.93 g sodium bicarbonate in 1 liter deionised water;
2) Wash buffer, pH 7.4
   6.07 g Tris, 0.2 g potassium chloride, 29.2 g sodium chloride in 800 ml deionised water adjusted to pH 7.4 with hydrochloric acid and made up to 1 liter;
3) Buffer for standard/sample diluent, pH 7.4
   0.37 g potassium chloride, 0.74 g disodium ethylenediaminetetra-acetate, 3 g Tris, 8.58 g sodium chloride in 800 mls deionised water adjusted to pH 7.4 and made up to 1 liter;
4) Standard/sample diluent
   200 ml of buffer (3) to which is added 0.2 g human albumin and 1 tablet of Complete® protease inhibitors (Boehringer Mannheim);
5) Citrate solution, pH 7.4
   2.94 sodium citrate dissolved in 800 ml deionised water adjusted to pH 7.4 with hydrochloric acid and made up to 1 liter;
6) Antibody conjugate reagent
   5 mls reagent (2), 6 mls Roti-Block® (Rotech Scientific, Milton Keynes, UK), 0.2 ml reagent (5), 0.012 g human serum albumin and 1 ml of the in-house anti-$cPLA_2$ IgG (as described herein)—alkaline phosphatase conjugate;
7) Luminescence reagent containing Lumi-Phos® 530 (buffered solution containing dioxetane Lumigen® PPD, fluorescer and surfactant) (obtained from Beckman Coulter, UK)

The assay is performed using 96 well microtitre plates according to the following procedure:

1) The capture antibody (obtained from The Binding Site. Birmingham. UK) was diluted 1:10 with saline and stored in 500 µl aliquots at −20° C. One aliquot of this antibody is added to 11.5 ml coating buffer, mixed and 100 µl of diluted capture antibody is pipetted into each well of a white microtitre plate to coat the wells of the plate with capture antibody. The plate is sealed and stored at 4° C. overnight. Prior to use, the plate is then washed four times with wash buffer pH 7.4 (reagent (2) as hereinbefore described).
2) The plate is blocked by pipetting into each well 300 µl of Roti-Block® diluted 1:2 with reagent (2). Blocking takes 90 minutes at 25° C. Blocking reagent is removed by washing four times with reagent (2).
3) Duplicate aliquots (100 µl) of sample or standard are then pipetted into each microtitre plate well and the plate incubated for 90 minutes at 25° C. The incubation is stopped by washing the plate four times with reagent (2).

4) The second antibody (the conjugated antibody, reagent (6)) is then added. Antibody is conjugated to alkaline phosphatase by standard techniques (Duncan et al., *Analytical Biochemistry* 132, 68–73). 100 µl of the antibody conjugate, reagent (6), is added to each well and the plate incubated for 90 minutes at 25° C.

5) At the end of this incubation, the plate is washed 8 times with reagent (2).

6) Luminescence is developed in the wells of the plate by adding 100 µl luminescence reagent (7) to each well and incubating for 20 minutes with shaking in a luminometer (Luminoscan Labsystems, Helsinki).

Figure 2:
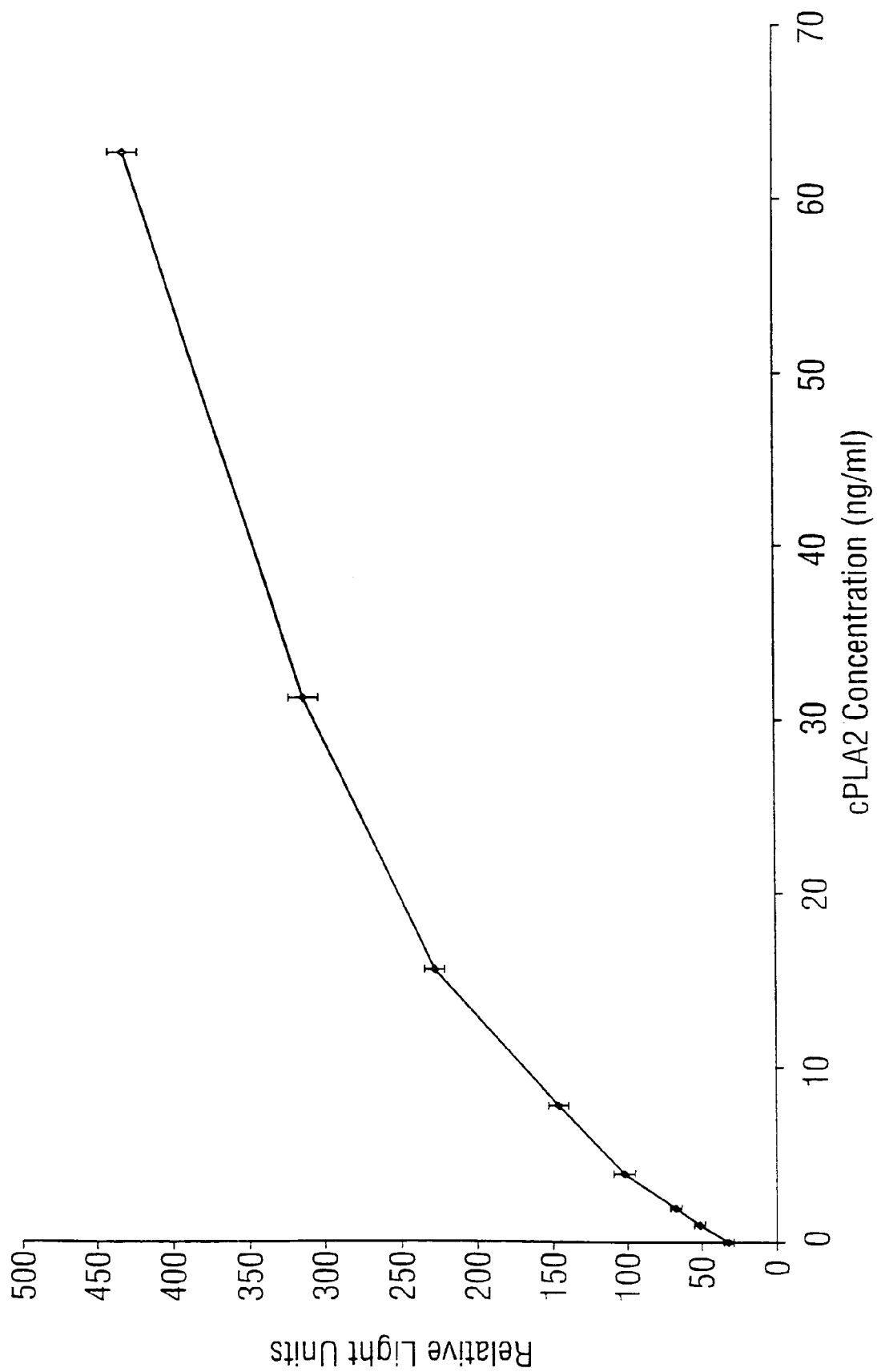
FIG. 2 depicts a calibration curve for an enzyme-linked immunoassay for type IV $cPLA_2$ protein, which uses a luminescence end point for protein detection.

7) Luminescence in relative light units for a given sample is measured and compared with that of standard type IV $cPLA_2$ preparations. The use of standard type IV $cPLA_2$ preparations can be used to derive a calibration curve for an assay for $cPLA_2$. FIG. 2 shows a calibration curve derived from 10 separate assays with the standard error of the mean marked.

8) Sample preparation

Prior to analysis, the frozen red blood cells were thawed, centrifuged at 10,000 g for 5 minutes and diluted 1:40 with sample diluent (reagent (4)).

9) Standard preparation

A U937 cell cytosol was utilised as a standard. This was prepared from U937 human monocyte culture (Clark et al., *Proc. Nat. Acad. Sci. USA*, 87, 7708–7712), Cells were harvested from culture, resuspended in standard/sample diluent, omitting the albumin content and with the addition of 11.6 g/100 ml sucrose. The cells were disrupted by nitrogen cavitation in a Parr bomb and the resulting preparation centrifuged at 150,000 g for 1 hour at 4° C. The supernatant, a U937 cell cytosol, was aliquoted and stored at −80° C. for standardisation. Western blot analysis of dilutions of this material allowed allocation of a value for type IV $cPLA_2$ content from the point at which type TV $cPLA_2$ was just detected by Western blot. The standard is stable at −80° C. All assays included internal quality control samples of an aliquoted red cell haemolysate.

10) Units for the estimation of type IV $cPLA_2$ in red cells haemolysates are µg $cPLA_2$ per g haemoglobin.

Haemoglobin amounts were estimated by diluting the sample to 0.04% ammonia and reading the optical density at 540 mm, standardised against haemoglobin of known concentration.

Within-batch percentage coefficient of variation (CV %), which is a measurement of relative variation, i.e. the standard deviation expressed as a percentage of the arithmetic mean, typically measured 8.6% and between-batch CV % typically measured 10.8%. These were measured at 9.0 ng $cPLA_2$ per g of haemoglobin (ng/gHb) and 9.7 ng/gHb respectively.

IV. Measurement of Type IV $cPLA_2$ Levels in Red Blood Cells in Various Patient Groups As an illustration of the clinical application of the measurement in red cells of type IV $cPLA_2$ protein or protein immunologically homologous to type IV $cPLA_2$, various blood samples were collected from groups of patients each with a defined psychiatric illness and from a control group. The samples from each patient group in this study were analysed using the ELISA method hereinbefore described. The patients within each group met stated criteria for their clinical diagnosis, as detailed below. Samples were collected using steps 1 to 7 hereinbefore described. Specimens were also collected and prepared omitting washing steps 4 to 5. This alternative shortened cell preparation method, employing only steps 1 to 3 and 6 to 7 was examined for its influence on the assayed levels of $cPLA_2$. Comparisons were made of samples given the full wash procedure and samples using the shortened procedure. No significant difference was found either within groups or combining the results in all groups when the two red cell preparation procedures were compared. The patients groups were as follows:

Group 1: Schizophrenia

49 Patients who met the DSM IV criteria for the diagnosis of schizophrenia (Diagnostic and Statistical Manual of Mental Disorders 4th Edition, American Psychiatric Association 1994);

36 Males and 13 females, age range 17 to 66 with mean age 37.3+/−11.9 years.

Group 2: Dyslexia

27 Volunteers with recognised criteria for identification of Dyslexia, i.e. a difference of 15 points or more between Wechsler Adult Intelligence Scale Revised (WAIS-R) pro-rated equivalent IQ (© The Psychological Corporation Limited 1986) and Wide Range Achievement Test score (WRAT) (Wilkinson © Wide Range Inc, 1993) or reaching a Bangor Dyslexia Test score (T. R. Miles in Dyslexia, The Pattern of Difficulties. Grenada, 1983) equal to or greater than 7;

17 Males and 10 females of age range 16 to 67 with mean age 35.4+/−13.2 years.

Group 3: Controls 51 volunteers comprised the control group;

25 Males and 26 females, age range 16 to 57 with mean age 35.4+/−12.4 years.

Figure 3A:
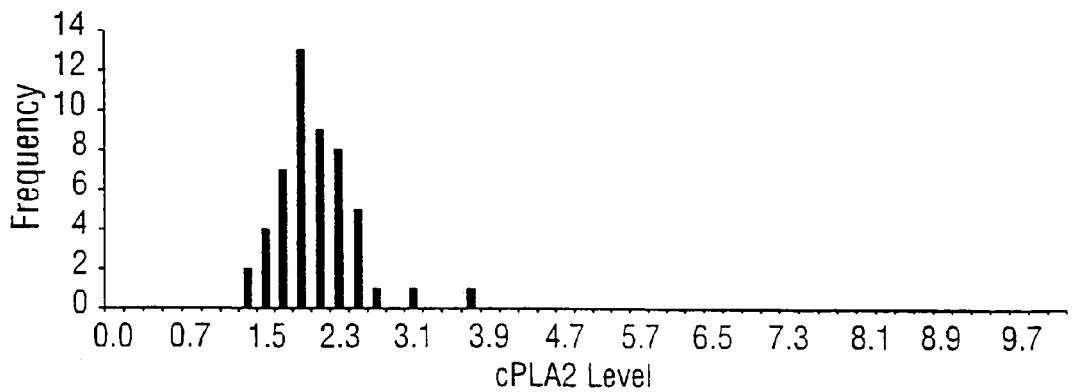
FIG. 3A depicts a frequency histogram of type IV $cPLA_2$ levels in the red blood cells of 51 healthy volunteers using an enzyme-linked immunoassay for type IV $cPLA_2$ protein.
Figure 3B:
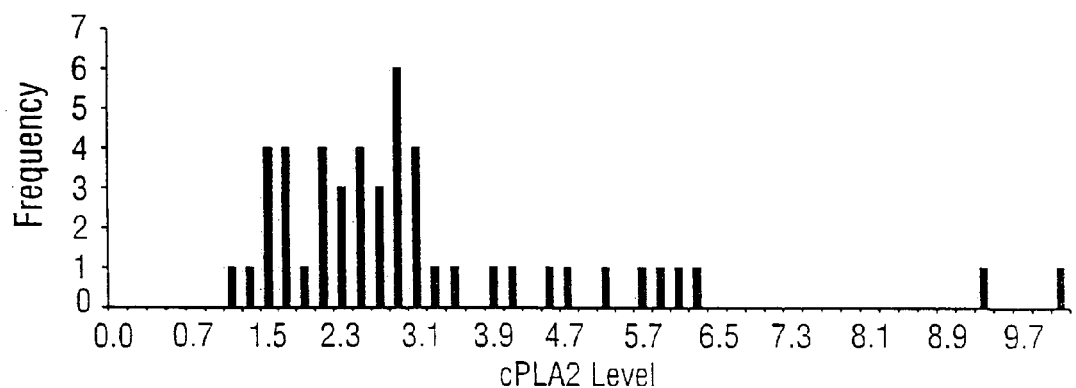
FIG. 3B depicts a frequency histogram of type IV $cPLA_2$ levels in the red blood cells of 49 patients who meet the DSM IV criteria for the diagnosis of schizophrenia using an enzyme-linked immunoassay for type IV $cPLA_2$ protein.
Figure 3C:
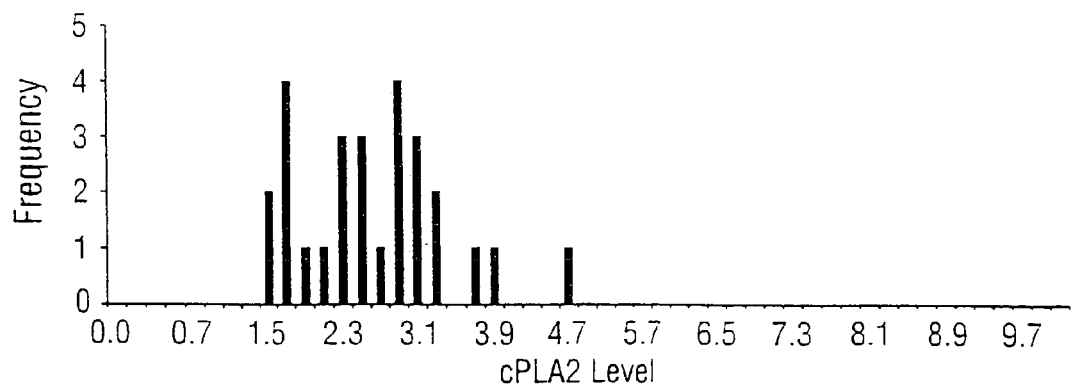
FIG. 3C depicts a frequency histogram of type IV $cPLA_2$ levels in the red blood cells of 27 volunteers with recognized criteria for identification of dyslexia using an enzyme-linked immunoassay for type IV cPLA$_2$ protein.

The results of the study are displayed in FIGS. 3A, 3B and 3C which show the frequency histogram of red cell type IV $cPLA_2$ or proteins or proteins immunologically homologous to type IV $cPLA_2$ in µg $cPLA_2$ per g haemoglobin (Hb) as estimated by the ELISA method hereinbefore described. FIGS. 3A, 3B and 3C illustrate, respectively, the control group, the schizophrenic group and the dyslexic group.

The distribution of the results of the assays for red cell type IV $cPLA_2$ or proteins or proteins immunologically homologous to type IV $cPLA_2$ measured as µg per g haemoglobin (Hb) was positively skewed (FIG. 3) and non-parametric tests were applied in analysis. Mann Whitney U test of the schizophrenia patient group and controls reveal a highly significant elevation of red cell $cPLA_2$ in the schizophrenia group compared with the control group (P<0.0001). There was a lesser elevation of red cell $cPLA_2$ in the dyslexic subjects compared with controls (P<0.001). Determination of a reference range encompassing 95% of the control group for red cell $cPLA_2$ permitted determination of an upper cut off point for the reference range for red cell $cPLA_2$ of 2.8 µg per g Hb. This is not an absolute value but is derived from the standardisation procedure used for these studies, as hereinbefore described.

Confirmation of the ELISA analysis of the type IV $cPLA_2$ proteins or proteins immunologically homologous to type IV $cPLA_2$ in the red cell haemolysates may be obtained by using SDS PAGE and western blot analysis using the techniques previously described. Samples from a patient in the control group and from a patient in the schizophrenic patient group (group 1) were subjected to further analysis using SDS PAGE and western blot. The group 1 sample was taken from a patient that had been shown by ELISA to have high levels of type IV cPLA$_2$ proteins or proteins immunologically homologous to type IV cPLA$_2$ in the red cell haemolysates.

Figure 4:
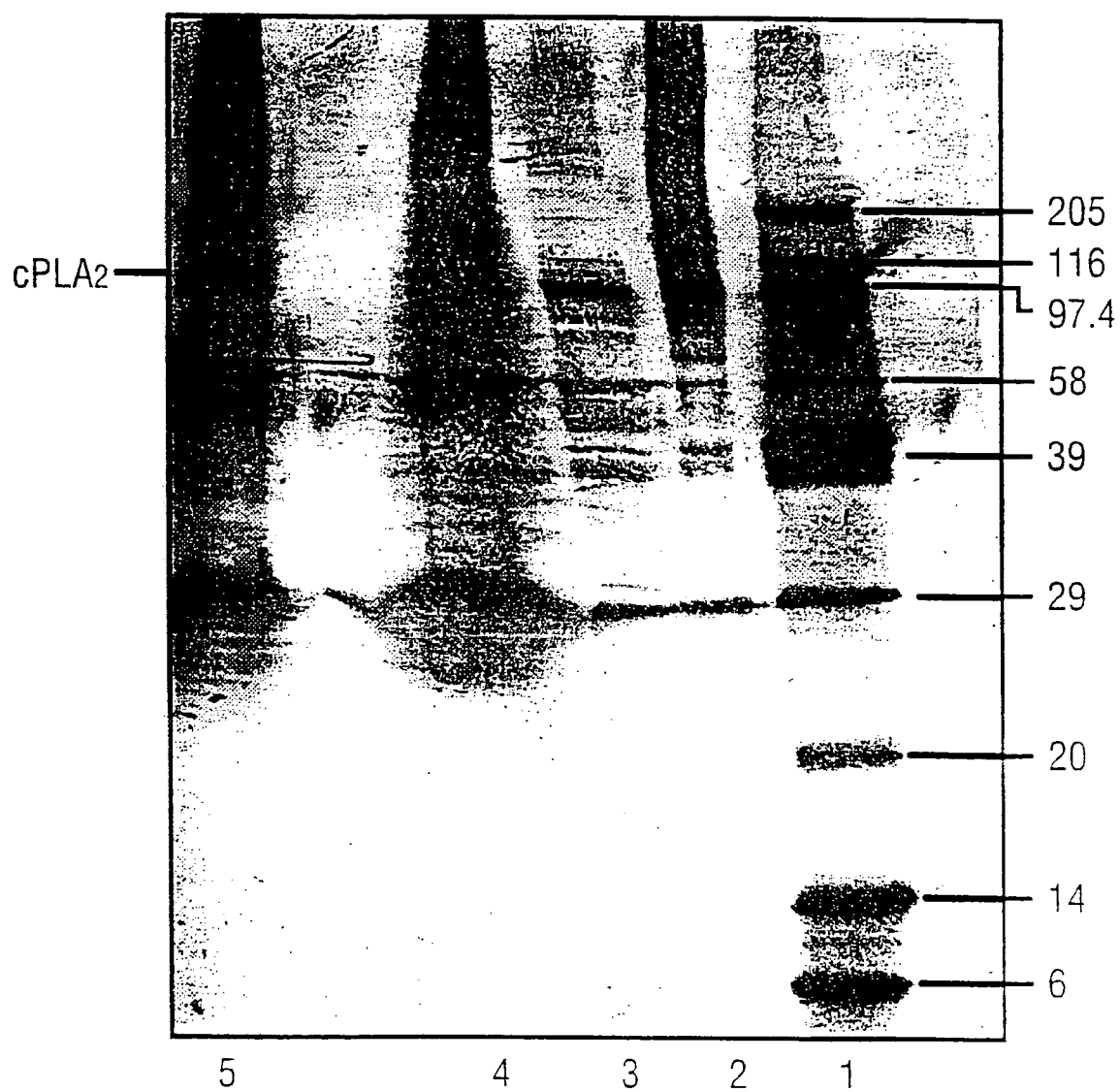
FIG. 4 demonstrates a western blot analysis of type IV cPLA$_2$ protein antigen in red cell hemolysates from a schizophrenia subject and a control subject. Lane 1: molecular weight markers. Lane 2: cytosol from insect cells infected with baculovirus expressing type IV cPLA$_2$. Lane 3: cytosol form human monocyte U937 cells containing a cPLA$_2$ protein. Lane 4: red cell hemolysate from a control subject. Lane 5: red cell hemolysate from a schizophrenia subject.

FIG. 4 illustrates the type IV cPLA$_2$ proteins or proteins immunologically homologous to type IV cPLA$_2$ in the red cell haemolysates, and the proteins observed in a red cell haemolysate from a control patient, as observed by SDS PAGE/western blot. Protein of the molecular weight of cPLA$_2$ protein from human monocyte U937 cells is observed in the haemolysate from the schizophrenic patient; there was no protein detected which had this molecular weight in the haemolysate from the control subject. The various samples in the western blot analysis shown in FIG. 4 are as follows:

Lane 1: Molecular weight markers
Lane 2: Cytosol from insect cells infected with baculovirus expressing type IV cPLA$_2$
Lane 3: Cytosol from human monocyte U937 cells containing a cPLA$_2$ protein
Lane 4: Red cell haemolysate from a control subject
Lane 5: Red cell haemolysate from a schizophrenia subject

What is claimed is:

1. An assay for detecting type IV cytosolic phospholipase A$_2$ (cPLA$_2$) protein or a protein immunologically homologous to type IV cPLA$_2$, the assay comprising
   i) obtaining a sample of red blood cells separated from whole blood, and
   ii) detecting said type IV cytosolic phospholipase A$_2$ (cPLA$_2$) protein or said protein immunologically homologous thereto in or on said red blood cells with an antibody to type IV cPLA$_2$ protein.

2. An assay according to claim 1 for use in the diagnosis of a disease in which dysfunction of cell signalling systems involving fatty acids having three or more carbon—carbon double bonds is implicated.

3. An assay according to claim 2 wherein said disease is a disease or disease process in which type IV cPLA$_2$ activity or concentration is altered from normal levels.

4. An assay according to claim 2 wherein said disease is a disease or disease process in which type IV cPLA$_2$ activity or concentration is increased relative to normal levels.

5. An assay according to claim 2 wherein the disease is schizophrenia, dyslexia, bipolar or manic depressive illness, cachexia or brain injury.

6. An assay according to claim 5 wherein the brain injury is stroke or mechanical brain injury.

7. An assay according to claim 1 for use in monitoring the effectiveness of medication administered to a patient suffering from a disease in which dysfunction of cell signalling systems involving fatty acids having three or more carbon—carbon double bonds is implicated.

8. An assay according to claim 1 for use in drug development for a disease in which dysfunction of cell signalling systems involving fatty acids having three or more carbon—carbon double bonds is implicated.

9. An assay according to claim 1 wherein the red blood cells are isolated from the human body.

10. An assay according to claim 1 wherein the type IV cPLA$_2$ protein or the protein immunologically homologous to type IV cPLA$_2$ has a molecular weight in the range 80 to 110 kDa or in the range 70 to 80 kDa or in the range 50 to 60 kDa.

11. An assay according to claim 1 wherein the type IV cPLA$_2$ protein or the protein immunologically homologous to type IV cPLA$_2$ has a molecular weight in the range 90 to 105 kDa or in the range 70 to 80 kDa or in the range 50 to 60 kDa.

12. An assay according to claim 1 wherein said proteins are detected using an antibody or antibodies raised against an epitope or epitopes from amino acids 1 to 216 of type IV cPLA$_2$ protein from human monocyte cells.

13. An assay according to claim 1 wherein said proteins are detected using an antibody or antibodies that recognise an epitope or epitopes from amino acids 82 to 749 of type IV cPLA$_2$ protein from human monocyte cells.

14. An assay according to claim 13, wherein two or more of the antibodies are used in combination or in sequence to detect the said proteins with the required specificity.

15. An assay according to claim 1 wherein said proteins are detected using an antibody or antibodies raised against an epitope or epitopes from amino acids 82 to 749 of type IV cPLA$_2$ protein from human monocyte or raised against an epitope or epitopes of a synthetic peptide matching amino acids 82 to 749 of type IV cPLA$_2$ protein from human monocyte cells.

16. An assay according to claim 13 or 15 wherein said epitope or epitopes are from a peptide sequence or sequences which comprise the catalytic centre of type IV cPLA$_2$ protein from human monocyte cells.

17. An assay according to claim 13 or 15 wherein said epitope or epitopes are from the peptide sequence of amino acids 241 to 260 of type IV cPLA$_2$ protein from human monocyte (U937) cells.

18. An assay according to claim 13 or 15 wherein the human monocyte cells are of the (U937) cell line.

19. A method of diagnosis of a disease in which dysfunction of cell signalling systems involving fatty acids having three or more carbon—carbon double bonds is implicated, said method comprising:
   i) obtaining a sample of red blood cells separated from whole blood, and
   ii) detecting type IV cytosolic phospholipase A$_2$ (cPLA$_2$) protein or a protein immunologically homologous to type IV cPLA$_2$ in or on red blood cells with an antibody to type IV cPLA$_2$ protein.

20. A method of monitoring the effectiveness of medication administered to a patient suffering from a disease in which dysfunction of cell signalling systems involving fatty acids having three or more carbon—carbon double bonds is implicated, said method comprising:
   i) obtaining a sample of red blood cells separated from whole blood, and
   ii) detecting type IV cytosolic phospholipase A$_2$ (cPLA$_2$) protein or a protein immunologically homologous to type IV cPLA$_2$ in or on red blood cells with an antibody to type IV cPLA$_2$ protein.

21. A method of drug development for a disease in which dysfunction of cell signalling systems involving fatty acids having three or more carbon—carbon double bonds is implicated, said method comprising:
   i) obtaining a sample of red blood cells separated from whole blood, and
   ii) detecting type IV cytosolic phospholipase A$_2$ (cPLA$_2$) protein or a protein immunologically homologous to type IV cPLA$_2$ in or on red blood cells with an antibody to type IV cPLA$_2$ protein.

22. An assay for detecting type IV cytosolic phospholipase A$_2$ (cPLA$_2$) protein or a protein immunologically homologous to type IV cPLA$_2$ comprising the steps of:
   i) collecting a sample of blood from a subject, and
   ii) detecting the proteins.

23. An assay according to claim 22 further comprising one or more of the following steps after obtaining the sample of red blood cells and prior to detecting the proteins:

(a) separating the red blood cells from other blood components, (b) disrupting the red blood cells, (c) separating the proteins using a protein separation technique.

24. An assay according to claim 23 wherein the red cells are disrupted by sonication, freezing, nitrogen cavitation or lysis.

\* \* \* \* \*